United States Patent
Grau et al.

(10) Patent No.: US 9,995,697 B1
(45) Date of Patent: Jun. 12, 2018

(54) X-RAY APPARATUS HAVING A MOTOR-DRIVEN TORQUE COMPENSATION AT THE DETECTOR CIRCLE OF THE GONIOMETER

(71) Applicant: Bruker AXS GmbH, Karlsruhe (DE)

(72) Inventors: Thorsten Grau, Karlsruhe (DE); Wolfgang Gehrlein, Ruelzheim (DE)

( * ) Notice: Subject to any disclaimer, the term of this patent is extended or adjusted under 35 U.S.C. 154(b) by 0 days. days.

(21) Appl. No.: 15/836,503

(22) Filed: Dec. 8, 2017

(30) Foreign Application Priority Data

Dec. 14, 2016 (DE) .................. 10 2016 224 940

(51) Int. Cl.
 *G01N 23/20* (2018.01)
(52) U.S. Cl.
 CPC .............................. *G01N 23/20016* (2013.01)
(58) Field of Classification Search
 CPC ................. G01N 23/207; G01N 23/20; G01N 23/20016; G01N 23/20025; G01N 23/20008; G01N 2223/076; G01N 2223/1016; G01N 23/201; G01N 23/223; G01N 2223/056; G01N 2223/316; G01N 2223/604; G01N 23/203; G01N 23/2206; G01N 2223/419; A61B 2034/107; A61B 34/20; A61B 34/30; A61B 34/32; A61B 34/37; A61B 17/16; A61B 34/70; A61B 2034/2046; A61B 17/1626; A61B 18/148; A61B 2018/00565; A61B 2018/00601; A61B 2090/066; A61B 2034/104; A61B 2034/2055
 USPC ..................................... 378/4, 15, 19, 62, 81
 See application file for complete search history.

(56) References Cited

U.S. PATENT DOCUMENTS

| 3,986,090 | A | * | 10/1976 | Hecker | ................ | A61B 6/4482 |
| | | | | | | 318/17 |
| 6,859,520 | B2 | * | 2/2005 | He | ................... | G01N 23/20016 |
| | | | | | | 378/71 |
| 7,242,745 | B2 | * | 7/2007 | He | ................... | G01N 23/20016 |
| | | | | | | 378/81 |

(Continued)

FOREIGN PATENT DOCUMENTS

| EP | 0161992 B1 | 11/1989 |
| EP | 1462795 A2 | 9/2004 |

(Continued)

*Primary Examiner* — Irakli Kiknadze
(74) *Attorney, Agent, or Firm* — Benoît & Côté Inc.

(57) ABSTRACT

For an x-ray apparatus comprising a goniometer with a detector circle rotatable about a goniometer axis, an actuator coupled to the detector circle for the motor-driven rotation thereof, a source arrangement with an x-ray source, a detector arrangement fastened to the detector circle and including an x-ray detector, and a sample position for a sample to be examined towards which the source arrangement and the detector arrangement are oriented, a compensation apparatus is provided that compensates for a torque about the goniometer axis produced by the weight of the detector arrangement on the detector circle. The compensation apparatus comprises a compensation motor coupled to the detector circle and a control device that actuates the compensation motor depending on a current position of the detector arrangement to apply a torque at least substantially equal and opposite to the torque produced by the detector arrangement.

15 Claims, 5 Drawing Sheets

(56) References Cited

U.S. PATENT DOCUMENTS

| | | | |
|---|---|---|---|
| 7,269,245 B2* | 9/2007 | He | G01N 23/20 |
| | | | 356/301 |
| 2007/0280426 A1* | 12/2007 | Saffer | A61B 6/4441 |
| | | | 378/198 |
| 2008/0123811 A1* | 5/2008 | Curtis | A61B 6/102 |
| | | | 378/91 |
| 2012/0213338 A1* | 8/2012 | Hartwich | A61B 6/4441 |
| | | | 378/197 |
| 2013/0287165 A1* | 10/2013 | Sharpless | A61B 6/032 |
| | | | 378/19 |

FOREIGN PATENT DOCUMENTS

| | | |
|---|---|---|
| EP | 1621873 A1 | 2/2006 |
| JP | 2001221752 A | 8/2001 |
| WO | 9113344 A1 | 9/1991 |

* cited by examiner

X-RAY APPARATUS HAVING A MOTOR-DRIVEN TORQUE COMPENSATION AT THE DETECTOR CIRCLE OF THE GONIOMETER

BACKGROUND OF THE INVENTION

Field of the Invention

This invention relates generally to the field of x-ray diffractometry and, more specifically, to goniometers to which x-ray diffraction components are mounted.

Description of the Related Art

A common type of x-ray apparatus comprises a goniometer with a detector circle which is rotatable about a goniometer axis, in particular wherein the goniometer axis extends in the horizontal direction, and an actuator, which is coupled to the detector circle, for the motor-driven rotation of the detector circle. A source arrangement which comprises an x-ray source is provided, as is a detector arrangement which is fastened to the detector circle, wherein the detector arrangement comprises an x-ray detector. The apparatus has a sample position for a sample to be examined, wherein the source arrangement and the detector arrangement are oriented towards the sample position, in particular wherein the sample position lies on the goniometer axis, and a compensation apparatus is provided, by means of which a torque that is produced by the weight of the detector arrangement is at least substantially compensated in relation to the goniometer axis on the detector circle.

X-ray radiation is used in multifaceted ways for the structure analysis of samples, in particular crystalline samples. In so doing, use is made of a goniometer in many measurement arrangements, in particular for x-ray diffraction. Using the goniometer, it is possible to modify the alignment of an x-ray source, a sample and an x-ray detector relative to one another, in particular in order to measure x-ray radiation, diffracted therewith, from the sample at various angles. Usually, a goniometer has a detector circle, on which an x-ray detector is fastened, and usually also a source circle, on which the x-ray source is fastened. The detector circle and source circle are rotatable in a motor-driven manner about a goniometer axis, on which the sample is usually also arranged. The goniometer axis is aligned horizontally in many cases.

An x-ray detector has a significant mass and therefore exerts a noticeable torque in relation to the goniometer axis. If the rotational position of the detector circle is set during an x-ray measurement by way of an actuator, the actuator needs to compensate this torque in order to maintain the rotational position of the detector circle. The forces required to this end increase the wear on the goniometer and on the actuator and also reduce the precision when setting the desired rotational position. A corresponding statement applies to the source circle.

EP 1 621 873 B1 has disclosed the practice, in the case of a goniometer of an XRD installation, of arranging a counterweight to the x-ray detector on the detector circle and arranging a counterweight to the x-ray source and the source-side optics on the source circle. The counterweights are intended to minimize the forces on the rotating components of the goniometer, which forces would otherwise reduce the rotational precision and cause excessive wear.

Although the mechanical load on a goniometer can be reduced using the counterweights, an adjustment position of a counterweight always only fits with a certain position of the x-ray detector or the x-ray source. By way of example, if the position of the x-ray detector is modified relative to the goniometer axis in order to modify the resolution of an x-ray diffraction measurement, it is necessary, as a matter of principle, also to readjust the counterweight. The adjustment of the counterweight is difficult and time-consuming and, moreover, harbors a certain risk of injury to the fitter carrying it out.

EP 1 462 795 B1 discloses an x-ray diffractometer, in which a rotatable detector arm is fastened to the detector circle of the goniometer such that an adjustment of the x-ray detector about two angles (gamma and theta) is possible.

JP 2001 221752 A describes an x-ray fluorescence arrangement having a detector arm that is repositionable about an angle theta. The rotational position of the detector arm is set with a main motor and an auxiliary motor removes play in the rotational position.

SUMMARY OF THE INVENTION

The invention is based on providing an x-ray apparatus with a compensation of torques on the detector circle of a goniometer in the case of a changeable position of the detector arrangement is simplified, in particular such that a compensation of torques is also possible in the case of a variable position during an ongoing x-ray measurement. This is achieved in a surprisingly simple and effective manner by way of an x-ray apparatus of the type set forth at the outset, which is characterized in that the compensation apparatus comprises a compensation motor, which likewise is coupled to the detector circle, for applying a torque in respect of the goniometer axis to the detector circle, and a control device for the compensation motor, said control device being embodied to actuate the compensation motor depending on a current position of the detector arrangement in such a way that the torque applied by the compensation motor is at least substantially equal and opposite to a torque in respect of the goniometer axis that is produced by the weight of the detector circle including the detector arrangement.

The invention involves engaging on the detector circle with two motors, namely, the actuator and a compensation motor. Using the actuator, the detector circle is brought into a respectively desired rotational position and kept there. Using the compensation motor, an additional torque is applied to the detector circle in order to compensate the torque of the detector arrangement (and possibly of further parts fastened to the detector circle) produced by the weight, provided that it has not yet been compensated by other measures such as counterweights.

Thus, the compensation motor ensures that the detector circle is approximately torque-free when the actuator adjusts or maintains a rotational position of the detector circle within the scope of an x-ray measurement (typically a diffraction measurement). As a result, the wear on the actuator is reduced. Likewise, the adjustment accuracy of the actuator is improved since elastic warpage is reduced.

The control device determines a suitable torque (or an associated value of a controlled variable of the compensation motor such as, e.g., an operating current) for the compensation motor from the current position of the detector arrangement, which is known to the control device.

The position of the detector arrangement is described by one or more position variables. Within the scope of determining the suitable torque, a calculation can be effectuated by means of the position variable(s), or else it is possible to read out or apply a previously stored value table (optionally also a value matrix) or characteristic (optionally also a characteristic field). Usually, the control device also actuates the actuator (and optionally one or more further actuators) for the x-ray measurement such that the control device knows the position of the detector arrangement, at least in part, from its dedicated control commands for the detector arrangement. To the extent that this is necessary, it is also possible to provide one or more sensors for determining the position or position variables of the detector arrangement. Typical position variables of the detector arrangement, which are taken into account within the scope of determining the suitable torque, are the angle Θ (theta, rotational position in relation to the goniometer axis), the angle Γ (gamma, rotational position in relation to a coplanar axis) and/or a distance AB in relation to the sample position. Position variables of the detector arrangement typically relate to a detection location for the x-ray radiation, for example the inlet opening of the x-ray detector. Alternatively, they may also relate to, for example, the center of mass of the detector arrangement. The information about the position of the detector arrangement optionally also comprises information about a setting of an auxiliary mechanism, by means of which the detector arrangement or the x-ray detector is aligned.

In principle, the suitable torque emerges from the horizontal distance of the center of mass of the detector circle (including parts fastened thereto, in particular the detector arrangement and optional counterweights) from the goniometer axis, the mass of the detector circle (including parts fastened thereto) and the gravitational acceleration. The location of the center of gravity of the (entire) detector circle is a function of the current position of the detector arrangement and therefore also determinable (in the case of a detector circle with a construction that is otherwise known, including parts fastened thereto) and able to be taken into account for the control. However, it is also possible to ascertain suitable torques belonging to respective positions of the detector arrangement by experiment and store these.

Within the scope of the invention, the compensation motor can be controlled by way of approximations without exactly determining the location of the center of gravity of the (entire) detector circle, which simplifies the control and already facilitates a very good torque compensation. By way of example, a useful approximation lies in assuming that the center of mass of the detector arrangement is at the detection location (inlet opening of the x-ray detector) such that the variables (e.g., Θ, Γ and AB) that are used for the x-ray measurement and describe the position of the detection location are used as if they describe the position of the center of mass of the detector arrangement which is actually relevant for the torque as a result of the weight.

As a rule, torques in relation to the goniometer axis that are caused by the weight of the (entire) detector circle can be reduced in terms of magnitude by at least 80%, and usually even by at least 95%, using the invention. Typically, the compensation is such that the actuator can operate within an intended interval of residual torque, within which the actuator does not yet have a noticeable adjustment error ("plateau region"). As a matter of principle, the compensation motor is continuously in operation during the use of the x-ray apparatus or of the goniometer.

An advantageous embodiment of the x-ray apparatus provides for the detector arrangement to be fastened to the detector circle in a manner pivotable about a coplanar axis, wherein the coplanar axis extends perpendicular to the goniometer axis and intersects the goniometer axis at the sample position. Pivoting of the x-ray detector about the coplanar axis (angle Γ) is often used in x-ray diffraction measurements of samples in order to increase a measurable solid angle range and it is accompanied by a significant change in the torque on the detector circle, and so taking account of this pivoting within the scope of the invention ensures particularly great unburdening of the goniometer and of the actuator. It is also possible to take account of other or further degrees of freedom (adjustment possibilities) of the detector arrangement within the scope of the invention, for example a rotation of the x-ray detector about the beam axis. Preferably, at least two degrees of freedom of the detector arrangement are taken account of within the scope of the invention.

In a preferred development of this embodiment, provision is made for a front cantilever part to be anchored to the detector circle, for a rear cantilever part to be mounted on the front cantilever part in a manner pivotable about the coplanar axis, for the detector arrangement to be fastened to the rear cantilever part and for provision to be made of a first further actuator for motor-driven rotation of the rear cantilever part. This construction for pivoting the detector arrangement about the coplanar axis is particularly simple.

Additionally, an advantageous embodiment has the detector arrangement fastened to the detector circle by way of a guide system, such that the detector arrangement can be displaced by means of the guide system toward the sample position or away from the sample position. In particular, the detector arrangement may be displaced perpendicular to the goniometer axis, along a displacement axis which intersects the sample position, and said detector arrangement can be locked at various displacement positions. By displacing the detector arrangement along the displacement axis (distance AB), it is possible to modify the spatial resolution of an x-ray measurement (with the same x-ray detector). Displacing the detector arrangement is likewise accompanied by a significant change in the torque on the detector circle, and so taking account of this pivoting within the scope of the invention ensures particularly great unburdening of the goniometer and of the actuator. If desired, provision can be made of a further actuator, by means of which the detector arrangement is displaceable on the guide system. It is likewise possible to provide a sensor for determining the displacement position.

An advantageous embodiment provides for the source arrangement to be fastened to a source circle of the goniometer, said source circle likewise being rotatable about the goniometer axis, and for the actuator or a second further actuator to be coupled to the source circle for motor-driven rotation of the source circle. As a result of the rotatable source circle, it is possible to modify the relative alignment of source arrangement and detector arrangement during a measurement without needing to rotate the sample. This is useful, e.g., for liquid samples. For the purposes of compensating torque on the source circle, one or more counterweights, substantially lying opposite the source arrangement with respect to the goniometer axis, are usually fastened to the source circle. Alternatively, or additionally, a further compensation motor can also be coupled to the source circle, in a manner analogous to the detector circle.

In a preferred embodiment, the compensation apparatus furthermore comprises one or more counterweights that are fastened to the detector circle and lie substantially opposite the detector arrangement in relation to the goniometer axis. As a result, an unburdening of the compensation motor can be achieved. For the purposes of determining the suitable torque for the compensation motor (in particular for determining the center of mass and the overall mass of the detector circle), it is necessary to take account of the counterweight or counterweights. The counterweights can assume a part of a torque to be compensated that changes only with rotation about the goniometer axis; the remaining part that can (also) be changed in a different way is compensated by the compensation motor.

In an alternative embodiment, the compensation apparatus does not use counterweights. As a result, the x-ray apparatus overall becomes lighter. Possibly difficult or dangerous handling of counterweights is dispensed with entirely.

In another embodiment, provision is made for the compensation motor to drive a shaft via a toothed belt and for the shaft to engage in an internal toothing of the detection circle with a pinion. This construction is particularly simple and reliable. Alternatively, other types of coupling are also possible, such as a direct drive.

In another advantageous embodiment, the compensation motor is coupled to the detection circle via a reduction gearing, in particular with a reduction ratio of 40:1 or higher. As result of the reduction, it is also possible to apply comparatively large forces to the detector circle with a high accuracy using a small motor. Reductions of 50:1 or higher, in particular approximately 100:1, are usually chosen in practice.

Another alternative embodiment has the compensation motor embodied as a DC motor, in particular as a brushless DC motor. Using the operating current as controlled variable (or measured variable), a torque to be produced (or produced torque) can easily can be set (or measured) directly. Alternatively, hydraulic or pneumatic motor systems may also be considered.

The scope of the present invention also includes a method for operating an x-ray apparatus, in particular an x-ray apparatus according to the invention as described above, wherein the x-ray apparatus comprises a goniometer with a detector circle which is rotatable about a goniometer axis, in particular wherein the goniometer axis extends in the horizontal direction, and an actuator, which is coupled to the detector circle, for the motor-driven rotation of the detector circle. The apparatus further includes a source arrangement which comprises an x-ray source, a detector arrangement which is fastened to the detector circle, wherein the detector arrangement comprises an x-ray detector and a sample position for a sample to be examined, wherein the source arrangement and the detector arrangement are oriented towards the sample position, in particular wherein the sample position lies on the goniometer axis. Also included is a compensation motor coupled to the detector circle, for applying a torque in respect of the goniometer axis to the detector circle, and a control device for the compensation motor. In this method, the control device actuates the compensation motor depending on a current position of the detector arrangement in such a way that the torque applied by the compensation motor is at least substantially equal and opposite to a torque about the goniometer axis that is produced by the weight of the detector circle, including the detector arrangement. The torque produced by the weight of the detector circle (including parts fastened thereto, in particular the detector arrangement and optional counterweights) is compensated by the compensation motor such that the detection circle for the actuator is always substantially torque-free. Changes in the torque to be compensated, which emerge from a changeable position of the detector arrangement, are captured by the control device and accordingly taken into account during the actuation of the compensation motor. As a result, the goniometer and actuator are unburdened, which improves the setting precision and reduces wear.

In a preferred variant of the method according to the invention, the control device takes account of a position variable $\Theta$ of the detector arrangement for controlling the compensation motor, where $\Theta$ is the angular position of the detector arrangement with respect to the goniometer axis, measured in relation to a first reference plane which contains the goniometer axis, in particular wherein the first reference plane is horizontal. The angle $\Theta$ (theta) is modified or captured for many x-ray diffraction experiments and has a great influence on the torque on the detector circle. It should be noted that the detector arrangement is usually inclined by $2\Theta$ in relation to the x-ray beam incident direction.

An advantageous development of this variant provides for the first reference plane to be horizontal and for the compensation motor to be controlled in such a way that the latter produces a torque $M_{KM}$ which has a contribution B1 approximately proportional to $\cos \Theta$. As a result, a shortening of the lever arm of the detector arrangement during pivoting about the goniometer axis is approximately accounted for (usually with an accuracy at least to within 20%, preferably with an accuracy at least to within 5%). In general, $M_{KM}$ also has a constant offset torque $C_0$ (for example, in order to take account of counterweights or friction).

In another variant, the control device takes account of a position variable $\Gamma$ of the detector arrangement for controlling the compensation motor, where $\Gamma$ is the angular position of the detector arrangement with respect to a coplanar axis, measured in relation to a second reference plane which contains the coplanar axis, in particular wherein the second reference plane extends perpendicular to the goniometer axis, and wherein the coplanar axis extends perpendicular to the goniometer axis and intersects the goniometer axis at the sample position. The angle $\Gamma$ (gamma) likewise is modified or captured for many x-ray diffraction experiments and has a great influence on the torque on the detector circle.

An advantageous development of this variant provides for the compensation motor to be controlled in such a way that the latter produces a torque $M_{KM}$ which has a contribution B2 approximately proportional to $\cos \Gamma$. As a result, a shortening of the lever arm of the detector arrangement during pivoting about the coplanar axis is approximately accounted for (usually with an accuracy at least to within 20%, preferably with an accuracy at least to within 5%). Typically, the contribution B2 is approximately proportional to $\cos \Theta$ at the same time, i.e., B2~$\cos \Gamma * \cos \Theta$.

In a yet another variant, the control device takes account of a position variable AB of the detector arrangement for controlling the compensation motor, where AB is the distance of the detector arrangement from the sample position. The distance AB is often modified in order to set the spatial resolution of the x-ray apparatus and has a great influence on the torque on the detector circle.

An advantageous development of this embodiment provides for the compensation motor to be controlled in such a way that the latter produces a torque $M_{KM}$ which has a contribution B3 approximately proportional to AB. As a result, a shortening or lengthening of the lever arm of the detector arrangement when displacing the detector arrangement toward the sample position or away from the sample position, for example by means of an above-described guide system, is approximately accounted for (usually with an accuracy at least to within 20%, preferably with an accuracy at least to within 5%). Typically, the contribution B3 is proportional to cos Θ at the same time, i.e., B3~AB*cos Θ or else B3~AB*cos Θ*cos Γ.

Furthermore, a preferred variant provides for a value table, a value matrix, a characteristic or characteristic field for a torque $M_{KM}$ that is to be set by the compensation motor or for a value of a controlled variable that is to be applied to the compensation motor to be stored in the control device depending on one or more position variables of the detector arrangement, and for the control device to apply or read out the value table, the value matrix, the characteristic or the characteristic field during the operation of the x-ray apparatus in order to determine the torque $M_{KM}$ to be set or the value of the controlled variable. The torque to be set or the value of the controlled variable to be applied can be determined in a simple and quick manner from the position variable or position variables with the aid of the value table, the value matrix, the characteristic or the characteristic field. There is no need for in situ considerations in relation to the position of the center of mass of the detector circle, which simplifies and accelerates the determination. If need be, an interpolation, in particular a linear interpolation, can be carried out between value entries/characteristic positions.

Further advantages of the invention emerge from the description and the drawings. Likewise, the features specified above and the features yet to be explained below may be used according to the invention, respectively, on their own or together in any combination. The shown and described embodiments should not be understood to make up a comprehensive list but instead have an exemplary character for the explanation of the invention.

BRIEF DESCRIPTION OF THE DRAWINGS

The invention is illustrated in the drawings and will be explained in more detail on the basis of exemplary embodiments. In the drawings.

DETAILED DESCRIPTION

Figure 1:
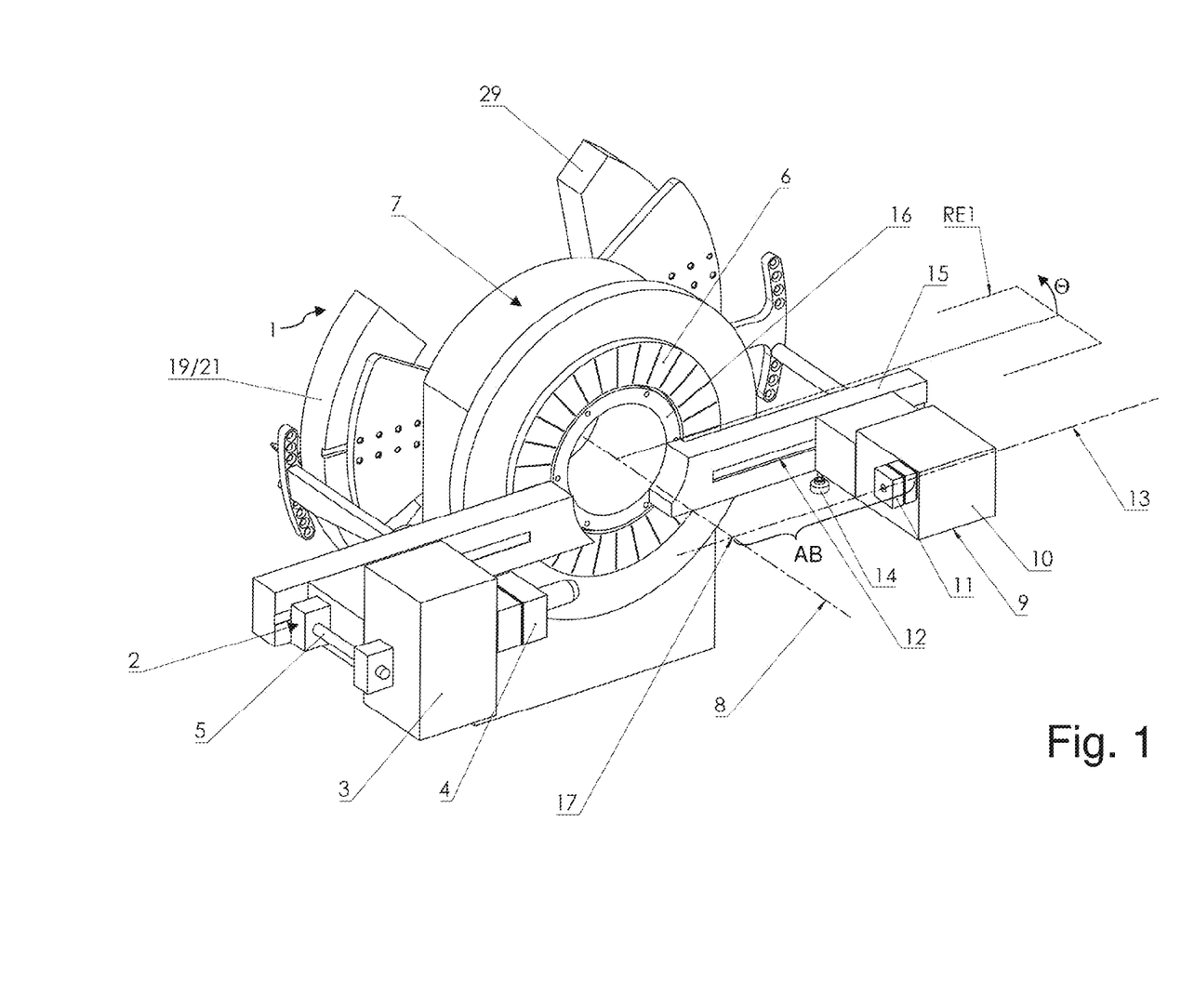
FIG. 1 shows a schematic oblique view of a first embodiment of an x-ray apparatus according to the invention, having an integral cantilever on the detector circle.

FIG. 1 shows, in a first embodiment, an x-ray apparatus 1 according to the invention for carrying out a method according to the invention. The x-ray apparatus 1 comprises a source arrangement 2, having an x-ray source 3, in this case an x-ray tube, arranged in front of which there are various x-ray optical elements 4 (here combination of x-ray mirrors, stops and a collimator), and having a holder mechanism 5. The source arrangement 2 is arranged on a source circle 6 of a goniometer 7, by means of which the source circle 6, and hence also the source arrangement 2, can be rotated in a motor-driven manner about a goniometer axis 8 that is horizontal in this case.

The x-ray apparatus 1 further comprises a detector arrangement 9, having an x-ray detector 10, arranged in front of which there are various x-ray optical elements 11 (here a combination of stops). The detector arrangement 9 is displaceable on a guide system 12 ("track") such that the detector arrangement 9 (or an associated detector window, which is covered in this case) is displaceable along a displacement axis 13. In this case, the displacement position of the detector arrangement 9 is manually adjustable and can be locked at any position by means of setscrews 14. Here, the guide system 12 is formed on an integral cantilever 15, which is fastened to a detector circle 16 of the goniometer 7. By means of the goniometer 7, it is possible to rotate the detector circle 16, and hence also the detector arrangement 9 arranged thereon, about the goniometer axis 8 in a motor-driven manner.

The source arrangement 2, or an x-ray beam produced thereby (not illustrated), and the detector arrangement 9 are oriented towards a sample position 17, which lies on the goniometer axis 8 in this case. It should be noted that the displacement axis 13 intersects the sample position 17. For the examination of a sample at the sample position 17 by means of x-ray diffractometry, the source arrangement 2 and the detector arrangement 9 are pivoted about the goniometer axis 8, and hence about the sample position 17, by means of the goniometer 7.

The detector arrangement 9 and the further parts fastened to the detector circle 16 have a significant mass, and so a torque is exerted on the detector circle 16 by the resultant weight. Expressed differently, the detector circle 16 overall (i.e. including the parts such as the cantilever 15 and the detector arrangement 9 fastened thereto) has a center of mass that is horizontally spaced apart from the goniometer axis 8 and, as a result thereof, attempts to turn the detector circle 16.

Figure 3:
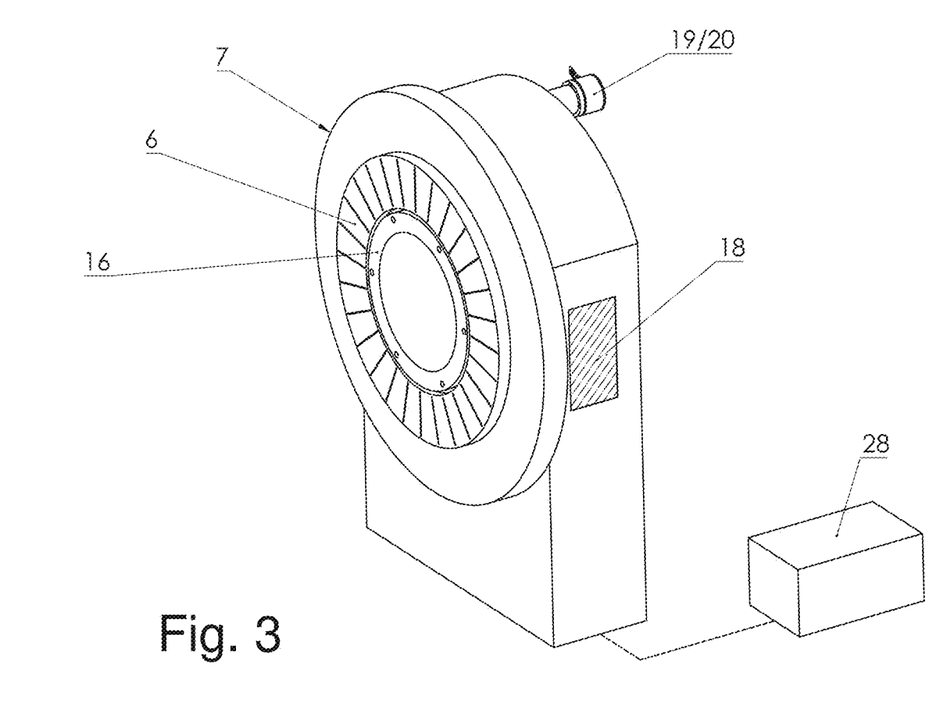
FIG. 3 shows a schematic, isolated illustration of the goniometer of the x-ray apparatus of FIG. 1.

As indicated in FIG. 3, the goniometer 7 has an actuator 18, by means of which the detector circle 16 is rotated to a desired rotational position and kept there. So that the actuator 18 need not work continuously against the weight of the detector arrangement (and other eccentric parts), the x-ray apparatus has a compensation apparatus 19. According to the invention, the compensation apparatus 19 comprises a compensation motor 20 which is coupled to the detector circle 16. Here, the compensation motor 20 is embodied as a brushless DC motor.

As is clear in turn from FIG. 1, the compensation apparatus 19 furthermore has counterweights 21 in this case, said counterweights being fastened to the detector circle 16 opposite to the detector arrangement 9 (in relation to the goniometer axis 8). It should be noted that the compensation motor 20 is covered by an upper part of the goniometer cover in FIG. 1.

Figure 2:
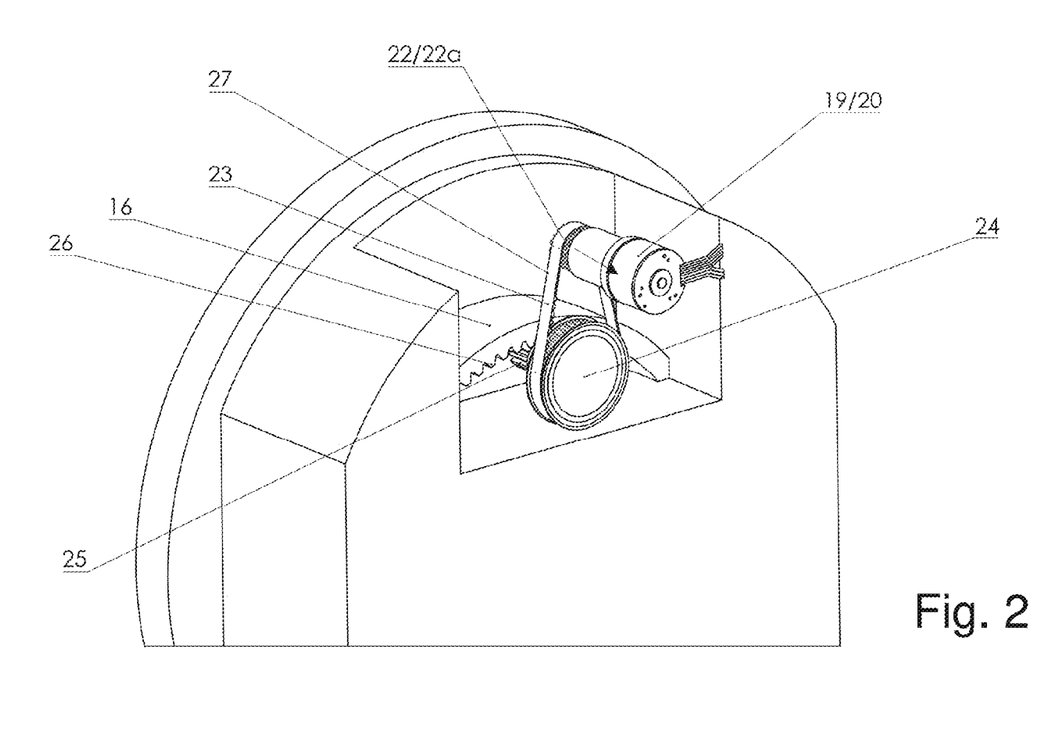
FIG. 2 shows a schematic, isolated illustration of the compensation motor, converting gearing and detector circle of the x-ray apparatus of FIG. 1.

As is clear from FIG. 2, the compensation motor 20 in this case has a motor shaft 22 having external toothing 22a. A toothed belt 23 (the toothing of which is only partly illustrated in FIG. 2) couples the motor shaft 22 to a shaft 24, on which a pinion 25 is formed. The pinion 25 engages into an internal toothing 26 (only illustrated in part in FIG. 2) on the detector circle 16. The gearing 27, which, in particular, is formed by the motor shaft 22 with the external toothing 22a, the shaft 24 with the pinion 25 and the internal toothing 26, transfers the rotation of the motor shaft 22 in a strongly reduced manner to the detector circle 16, here with a reduction ratio of approximately 50:1 (i.e., a rotation of the motor shaft 22 corresponds to 1/50 rotation of the detector circle 16).

It should be noted that the compensation motor 20 is independent of the actuator. The compensation motor 20 serves to make the detector circle 16 substantially torque-free for the actuator.

Referring to FIG. 1, the counterweights 21 provide good compensation of a torque contribution of the cantilever 15 (and other non-displaceable parts of the detector circle 16). A rotation of the detector circle 16 about the goniometer axis 8 (cf. angle Θ, theta) changes the horizontal distance of the counterweights 21 and of the cantilever 15 from the goniometer axis 8 to the same extent. By contrast, the torque contribution by the detector arrangement 9 also depends on the displacement position along the displacement axis 13 (cf. distance AB from the sample position 17). Therefore, the torque contribution of the detector arrangement 9 cannot be compensated by fixedly installed counterweights 21. The torque contribution of the detector arrangement 9, as well as any other uncompensated torque contributions of other parts installed on the detector circle 16, is compensated for by the compensation motor.

As schematically illustrated in FIG. 3, the x-ray apparatus has an electronic control device 28, which is connected to the goniometer 7. By way of example, the control device 28 can be realized by means of a desktop computer. Firstly, the control device 28 provides control commands to the actuator 18 within the scope of the programmed x-ray measurement in order to set the rotational position of the detector circle 16 (and also the source circle 6). Therefore, the control device 28 knows the current rotational position (angle position Θ, theta, measured here against a first, horizontal reference plane RE1 which contains the goniometer axis 8, as shown in FIG. 1) of the detector circle 16 or of the detector arrangement 9, with Θ (theta) being approximately 0° in the position shown here. Furthermore, the displacement position (distance AB between sample position 17/goniometer axis 8 and the detector window of the detector arrangement 9) of the detector arrangement 9 is made known to the control device 28 (for example by manual input after a manual readout of the position using the naked eye or else by reading a position sensor, not illustrated in any more detail). Using these position variables, and with an otherwise given construction of the x-ray apparatus, the control device 28 can ascertain a suitable compensation torque or a corresponding control current for the compensation motor 20 and apply the latter to the compensation motor 20.

In the shown embodiment, cf. FIG. 1, the source circle 6 also has counterweights 29 which lie opposite the source arrangement 2 (in relation to the goniometer axis 8). Since the source arrangement 2, as a rule, is only rotated about the goniometer axis 8 together with the counterweights 29 and is otherwise not adjusted, a good torque compensation can be achieved here by counterweights 29 that are securely installed on the source circle 6.

Figure 4:
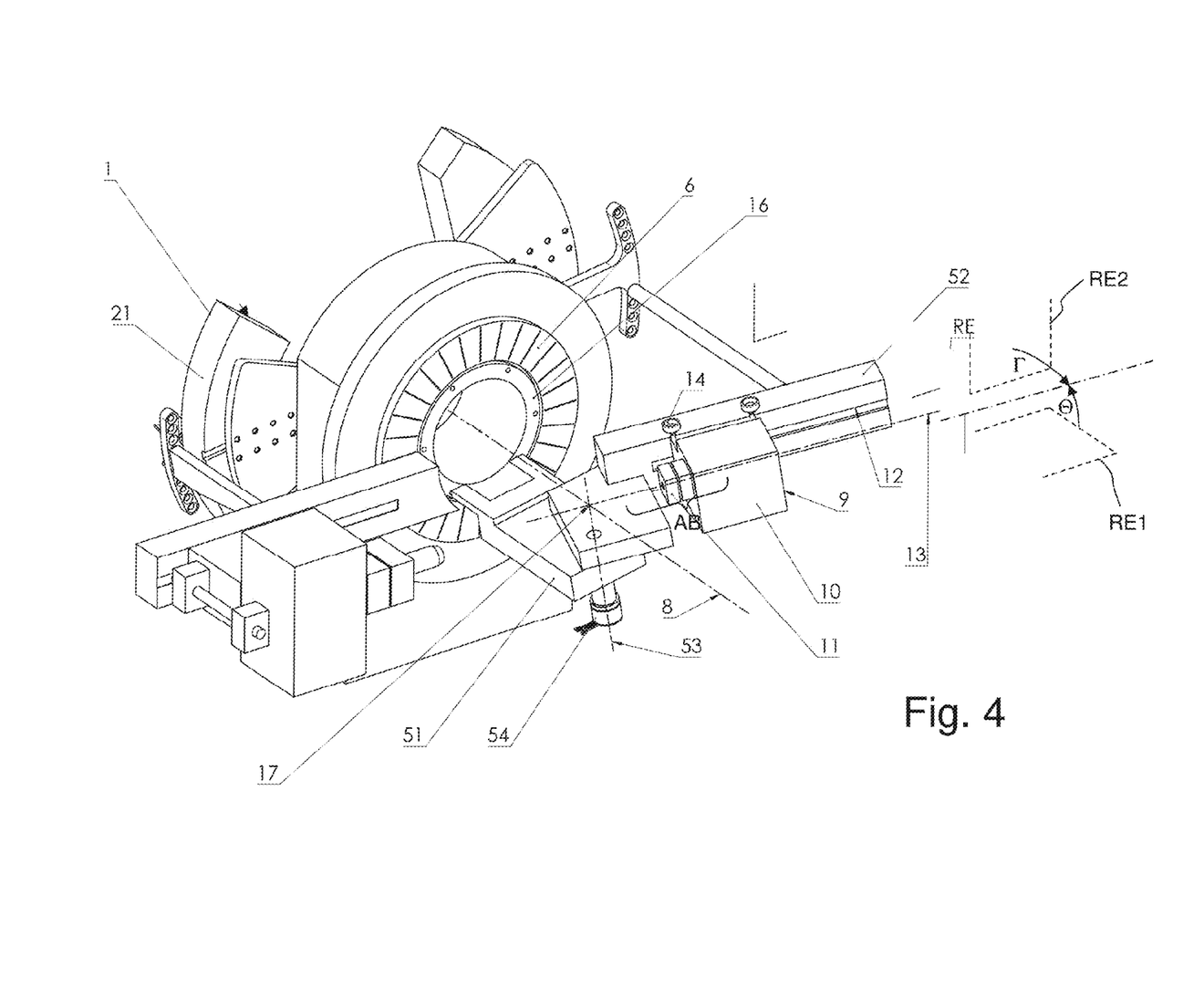
FIG. 4 shows a schematic oblique view of a second embodiment of an x-ray apparatus according to the invention, having a two-part cantilever on the detector circle.

FIG. 4 shows a second embodiment of an x-ray apparatus 1 according to the invention for use in a method according to the invention, which x-ray apparatus is similar to the x-ray apparatus of FIG. 1. Therefore, it is predominantly the essential differences from the embodiment of FIG. 1 that are explained.

Here, attached to the detector circle 16 there is a front, first cantilever part 51, hinged on which in a manner rotatable about a coplanar axis 53 there is a rear, second cantilever part 52. The rotational position (cf. angle Γ, gamma) in relation to the coplanar axis 53 can be set by way of a first further actuator 54. The latter is actuated by the electronic control device (not illustrated). The coplanar axis 53 extends perpendicular to the goniometer axis 8 and intersects the goniometer axis 8 at the sample position 17. The guide system 12, by means of which the detector arrangement 9 can be displaced along the displacement axis 13, is arranged on the second cantilever part 52.

As a result of the additional pivoting option of the detector arrangement 9 about the coplanar axis 53 (angle Γ, gamma), additional solid angle regions are accessible during an x-ray diffraction measurement. A change in torque on account of pivoting the detector arrangement 9 through an angle Γ (gamma) cannot be completely canceled out in this case by the counterweights 21; only the non-pivoting first cantilever part 51 can be compensated by the counterweights 21. Therefore, this embodiment also has a compensation motor (once again covered by the upper part of the goniometer cover in FIG. 4; however, cf. e.g., FIG. 3) which is coupled to the detector circle 16.

A counter-torque that is suitable for the compensation motor can be determined by means of the position variables Θ (theta, pivoting of the detector arrangement 9 about the goniometer axis 8, measured in relation to the first horizontal reference plane RE1), Γ (gamma, pivoting of the detector arrangement 9 about the coplanar axis 53, measured in relation to a second reference plane RE2, which is perpendicular to the goniometer axis 8 in this case and contains the coplanar axis 53) and AB (distance between the detector window of the detector arrangement 9 and the sample position 17). The current rotational position in respect of Γ (gamma), approximately 20° as shown here, is already known to the control device in this case as it is set by way of the control device. A corresponding statement applies to the current rotational position in respect of Θ (theta), approximately 10° as shown here.

It should be noted that, in the case of large angles Γ (gamma) of over 90°, there is a change in the sign of the torque on the detector circle 16 which is caused by the detector apparatus 9. Accordingly, the compensation motor is embodied for a bidirectional application of force.

Figure 5:
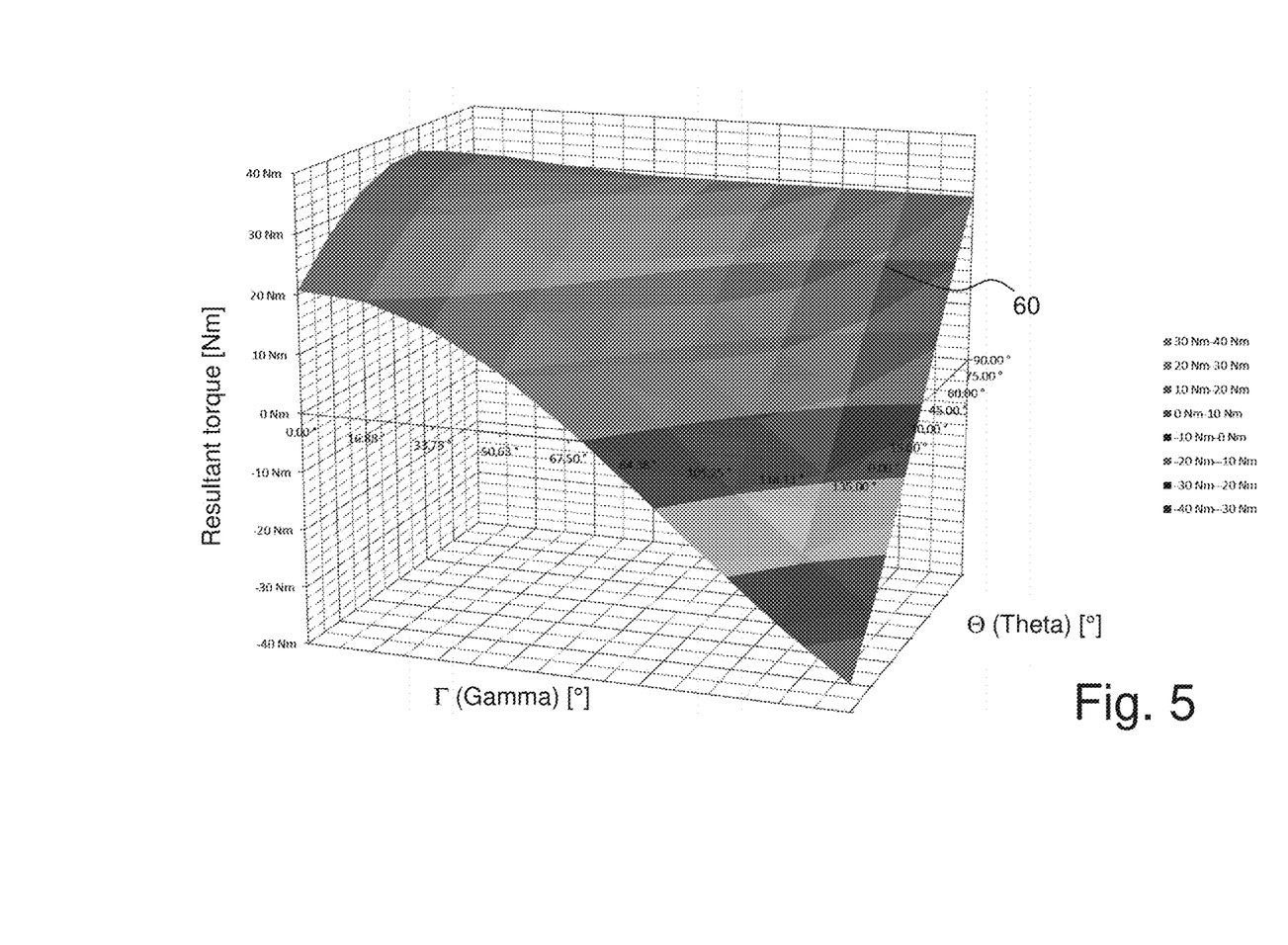
FIG. 5 shows a characteristic field for actuating the x-ray apparatus of FIG. 4.

FIG. 5 shows a typical characteristic field 60, as may be used within the scope of the invention by a control device according to the embodiment of an x-ray apparatus of FIG. 4. The field 60 specifies the torque (resultant torque about the goniometer axis, plotted upward) that must be compensated by the compensation motor, depending on the position variable angle Γ (gamma, plotted to the right) and the position variable angle Θ (theta, plotted to the back). In order to compensate this resultant torque, the compensation motor must apply −1 times said torque on the detector circle as torque $M_{KM}$ to be set. If the force characteristic of the compensation motor is known, it is then possible to determine and apply a control current for the compensation motor by means of the read-out torque of the characteristic field. The shown characteristic field 60 applies here for a specific distance AB between the detector arrangement and the sample position; further characteristic fields can be stored and used for other distances AB, or a three-dimensional characteristic field is stored and used (not depicted in any more detail).

In the simplest case, the characteristic field 60 is determined experimentally by virtue of the torque acting on the goniometer axis (without the compensation motor) being measured in advance for the various positions of the detector arrangement that are possible within the scope of the envisaged x-ray measurements. Alternatively, the acting torque can also be calculated, for example by way of the positions of centers of mass and the horizontal distances thereof from the goniometer axis. In general, approximately the following dependencies of the acting torque and the position variables occur:

a) constant components (independent of the position variables), for example caused by friction;

b) components proportional to cos Θ; these are caused by all parts that rotate about the goniometer axis and that are fastened to the detector circle;

c) components proportional to cos Γ, these are caused by all parts that rotate about the coplanar axis and that are fastened to the detector circle;

d) components proportional to AB; these are caused by all parts that are displaceable along the displacement axis and that are fastened to the detector circle.

It should be noted that some parts which are fastened to the detector circle may contribute to one or more of the aforementioned categories. Thus, in FIG. 4, the first cantilever part 51 causes a contribution (only) proportional to cos Θ, the second cantilever part 52 causes a contribution proportional to cos Θ*cos Γ and the detector arrangement 9 causes a contribution proportional to AB*cos Θ*cos Γ. The absolute contribution then depends further on the mass of the respective parts.

For the embodiment in FIG. 1, the cantilever 15 causes a contribution (only) proportional to cos Θ and the detector arrangement 9 causes a contribution proportional to AB*cos Θ.

For the embodiment of FIG. 4, a torque $M_{KM}$, which is representable as follows, approximately emerges for the compensation motor as a function of the position variables:

$$M_{KM} = A0 + A1^* \cos \Theta + A2^* \cos \Theta^* \cos \Gamma + A3^* AB^* \cos \Theta^* \cos \Gamma \quad (\text{Eq. 1})$$

where A0, A1, A2 and A3 are constants related to the x-ray apparatus. By rewriting, the following, in particular, emerges from equation 1:

$$M_{KM} = A0 + B1 \quad (\text{Eq. 2})$$

with $B1 = [A1 + A2^* \cos \Gamma + A3^* AB^* \cos \Gamma]^* \cos \Theta$ (Eq. 3)

where B1 is a contribution proportional to cos Θ.
Equation 1 can also be rewritten as follows:

$$M_{KM} = A0 + A1^* \cos \Theta + B2 \quad (\text{Eq. 4})$$

with $B2 = [A2^* \cos \Theta + A3^* AB^* \cos \Theta]^* \cos \Gamma$ (Eq. 5)

where B2 is a contribution proportional to cos Γ.
Furthermore, equation 1 can be rewritten as follows:

$$M_{KM} = A0 + A1^* \cos \Theta + A2^* \cos \Theta^* \cos \Gamma + B3 \quad (\text{Eq. 6})$$

with $B3 = [A3^* \cos \Theta^* \cos \Gamma]^* AB$ (Eq. 7)

where B3 is a contribution proportional to AB. The data stored in the characteristic field 60 approximately follow these dependencies. It should be noted that, depending on the construction of the x-ray apparatus, fewer, more or other terms than those stated for $M_{KM}$ in equation 1 may occur, as a result of which the terms in contributions B1, B2, B3 may also change.

As an alternative to determining $M_{KM}$ by way of characteristic fields, it is possible, for example, to determine the constants (A0, A1, A2, A3 in the example above) that occur for the torques in the model (cf. equation 1 in the example above) and store these in the control device, and calculate the torque $M_{KM}$ for the compensation motor using the model and the respectively present position parameters.

The invention claimed is:

1. An x-ray apparatus comprising:
a goniometer with a detector circle which is rotatable about a goniometer axis;
an actuator coupled to the detector circle, for the motor-driven rotation of the detector circle;
a source arrangement comprising an x-ray source;
a detector arrangement fastened to the detector circle, wherein the detector arrangement comprises an x-ray detector;
a sample position for a sample to be examined, wherein the source arrangement and the detector arrangement are oriented towards the sample position; and
a compensation apparatus that compensates a first torque about the goniometer axis that is produced by the weight of the detector arrangement on the detector circle, wherein the compensation apparatus comprises a compensation motor coupled to the detector circle for applying a torque about the goniometer axis to the detector circle and a control device for the compensation motor, said control device actuating the compensation motor depending on a current position of the detector arrangement in such a way that the torque applied by the compensation motor is at least substantially equal and opposite to said first torque.

2. The x-ray apparatus as claimed in claim 1, wherein the detector arrangement is fastened to the detector circle in a manner pivotable about a coplanar axis, wherein the coplanar axis extends perpendicular to the goniometer axis and intersects the goniometer axis at the sample position.

3. The x-ray apparatus as claimed in claim 2, wherein a front cantilever part is anchored to the detector circle and a rear cantilever part is mounted on the front cantilever part in a manner pivotable about the coplanar axis, and wherein the detector arrangement is fastened to the rear cantilever part and a first further actuator is provided for motor-driven rotation of the rear cantilever part.

4. The x-ray apparatus as claimed in claim 1, wherein the detector arrangement is fastened to the detector circle by way of a guide system such that the detector arrangement can be displaced by the guide system toward the sample position or away from the sample position along a displacement axis which intersects the sample position, and wherein said detector arrangement can be locked at various displacement positions.

5. The x-ray apparatus as claimed in claim 1, wherein the source arrangement is fastened to a source circle of the goniometer, said source circle being rotatable about the goniometer axis, and wherein the actuator, or a second actuator, is coupled to the source circle for motor-driven rotation thereof.

6. The x-ray apparatus as claimed in claim 1, wherein the compensation apparatus excludes counterweights.

7. The x-ray apparatus as claimed in claim 1, wherein the compensation motor comprises a DC motor.

8. A method for operating an x-ray apparatus comprising a goniometer with a detector circle which is rotatable about a goniometer axis, an actuator coupled to the detector circle for the motor-driven rotation of the detector circle, a source arrangement comprising an x-ray source, a detector arrangement which is fastened to the detector circle and comprises an x-ray detector, and a sample position for a sample to be examined, such that the source arrangement and the detector arrangement are aligned with the sample position, the method comprising:
providing a compensation motor coupled to the detector circle that applies a torque about the goniometer axis to the detector circle; and
actuating the compensation motor with a control device depending on a current position of the detector arrangement such that the torque applied by the compensation motor is at least substantially equal and opposite to a torque about the goniometer axis that is produced by the weight of the detector arrangement.

9. The method as claimed in claim 8, wherein the control device takes account of a position variable $\Theta$ of the detector arrangement for controlling the compensation motor, where $\Theta$ is an angular position of the detector arrangement with respect to the goniometer axis, measured relative to a first reference plane which contains the goniometer axis.

10. The method as claimed in claim 9, wherein the first reference plane is horizontal and wherein the compensation motor is controlled in such a way that it produces a torque $M_{KM}$ which has a contribution B1 approximately proportional to $\cos \Theta$.

11. The method as claimed in claim 8, wherein the control device takes account of a position variable $\Gamma$ of the detector arrangement for controlling the compensation motor, where $\Gamma$ is an angular position of the detector arrangement relative to a coplanar axis, measured relative to a second reference plane which contains the coplanar axis, and wherein the coplanar axis extends perpendicular to the goniometer axis and intersects the goniometer axis at the sample position.

12. The method as claimed in claim 11, wherein the compensation motor is controlled in such a way that it produces a torque $M_{KM}$ which has a contribution B2 approximately proportional to $\cos \Gamma$.

13. The method as claimed in claim 8, wherein the control device takes account of a position variable AB of the detector arrangement for controlling the compensation motor, where AB is a distance of the detector arrangement from the sample position.

14. The method as claimed in claim 13, wherein the compensation motor is controlled in such a way that it produces a torque $M_{KM}$ which has a contribution B3 approximately proportional to AB.

15. The method as claimed in claim 8, wherein a value table, a value matrix, a characteristic or characteristic field is stored in the control device depending on one or more position variables of the detector arrangement, and wherein the control device applies or reads out the value table, the value matrix, the characteristic or the characteristic field during the operation of the x-ray apparatus in order to determine a torque $M_{KM}$ to be set or the value of a controlled variable to be applied to the compensation motor.

* * * * *